US009005181B2

(12) United States Patent
Lynn et al.

(10) Patent No.: US 9,005,181 B2
(45) Date of Patent: Apr. 14, 2015

(54) STERILE OPENABLE ACCESS PORT AND CONTAINERS INCLUDING THE SAME

(71) Applicant: Fenwal, Inc., Lake Zurich, IL (US)

(72) Inventors: Daniel Lynn, Spring Grove, IL (US); Richard L. West, Lake Villa, IL (US); Bryan Blickhan, Libertyville, IL (US); Phoung Tran, Palatine, IL (US); Shawn Davis, Bristol, WI (US)

(73) Assignee: Fenwal, Inc., Lake Zurich, IL (US)

( * ) Notice: Subject to any disclaimer, the term of this patent is extended or adjusted under 35 U.S.C. 154(b) by 177 days.

(21) Appl. No.: 13/760,842

(22) Filed: Feb. 6, 2013

(65) Prior Publication Data

US 2013/0237946 A1 Sep. 12, 2013

Related U.S. Application Data

(60) Provisional application No. 61/608,799, filed on Mar. 9, 2012.

(51) Int. Cl.

| | |
|---|---|
| ***A61M 5/32*** | (2006.01) |
| ***A61B 19/00*** | (2006.01) |
| ***A61J 1/14*** | (2006.01) |
| ***A61J 1/18*** | (2006.01) |
| *A61J 1/10* | (2006.01) |

(52) U.S. Cl.

CPC . *A61J 1/1406* (2013.01); *A61J 1/10* (2013.01); *A61J 1/1475* (2013.01); *A61J 1/18* (2013.01); *A61J 2001/1431* (2013.01); *A61J 2001/1487* (2013.01); *Y10S 604/905* (2013.01)

(58) Field of Classification Search

CPC ..................................................... A61J 1/1406

USPC .......................................... 604/415, 905, 326

See application file for complete search history.

(56) References Cited

U.S. PATENT DOCUMENTS

| | | | |
|---|---|---|---|
| 3,327,709 A | 6/1967 | Nehring et al. | |
| 5,308,403 A * | 5/1994 | Yam et al. | 134/7 |
| 5,391,163 A | 2/1995 | Christine et al. | |
| 6,138,849 A * | 10/2000 | Roemer et al. | 215/48 |

(Continued)

FOREIGN PATENT DOCUMENTS

| | | |
|---|---|---|
| CH | 635 245 A5 | 4/1980 |
| DE | 198 42 960 A1 | 3/2000 |

(Continued)

OTHER PUBLICATIONS

European Search Report, dated Jun. 13, 2013, for Appln. No. 131567608.3, filed Feb. 26, 2013.

*Primary Examiner* — Tatyana Zalukaeva
*Assistant Examiner* — Kai Weng
(74) *Attorney, Agent, or Firm* — Cook Alex Ltd.

(57) ABSTRACT

A connector for providing sterile access to a flexible container is provided that comprises a tubular member having a first portion and a second portion, each of the first portion and the second portion having an open end. The first portion and second portion are joined to each other by a frangible segment, with each of the first portion and the second portion having a gripable surface associated therewith that is configured to facilitate the application of torsional force to the tubular member at the frangible segment. Upon the application of a sufficient amount of torsional force, the frangible segment will break, permitting the first and second portions to be separated from each other.

9 Claims, 4 Drawing Sheets

(56) References Cited

U.S. PATENT DOCUMENTS

| | | | | |
|---|---|---|---|---|
| 6,179,821 | B1 * | 1/2001 | Caspary et al. | 604/403 |
| 6,203,535 | B1 | 3/2001 | Barney et al. | |
| 6,273,307 | B1 * | 8/2001 | Gross et al. | 222/566 |
| 6,485,479 | B1 | 11/2002 | Knierbein | |
| 6,605,076 | B1 * | 8/2003 | Jepson et al. | 604/539 |
| 7,350,669 | B2 | 4/2008 | Rani | |
| 2003/0075469 | A1 | 4/2003 | Herbert | |

FOREIGN PATENT DOCUMENTS

| | | | |
|---|---|---|---|
| DE | 10039474 | C1 | 2/2002 |
| EP | 0 830 874 | B1 | 9/1997 |
| EP | 0830874 | A2 | 3/1998 |
| EP | 1 765 254 | B1 | 5/2005 |
| EP | 2 253 298 | A1 | 5/2010 |
| EP | 2388042 | A2 | 11/2011 |
| FR | 2873102 | A1 | 7/2004 |
| FR | 2 948 289 | | 7/2009 |

* cited by examiner

STERILE OPENABLE ACCESS PORT AND CONTAINERS INCLUDING THE SAME

FIELD OF THE DISCLOSURE

This disclosure relates generally to a sterile connector or sterile openable access port that allows for establishing flow communication with a container filled with a medical fluid, and, in particular, to a sterile connector with a pierceable membrane having a cover portion for maintaining the sterility of the connector, the cover portion being formed integrally with the remainder of the connector, and having a frangible segment of weakness that, upon manipulation, breaks to permit removal of the cover and access to the pierceable membrane. This disclosure also relates to containers, typically medical containers, including such connectors or ports.

BACKGROUND

The administration of medical solutions is commonly effected through the use of flexible solution containers that have one or more sterile connectors or access ports which may be sealed by pierceable membrane elements. The pierceable membranes act to seal the contents of the container until access is required, with the membrane being pierced through the use of, e.g., a spike of an associated tubing set or a hypodermic needle. The spike may be manipulated to penetrate the membrane to provide fluid communication between the hollow interior of the spike and the interior of the fluid container, thus permitting the flow of liquid through the access port in a convenient and efficient fashion.

In order to avoid contamination of the solution within the container, the access port is typically provided with a cover or closure that seals the port and protects the membrane against contamination prior to the membrane being pierced by the spike.

By way of the present disclosure, a sterile connector or access port is provided that has an integral cover that is removed prior to use to permit access to the pierceable membrane which facilitates the efficient manufacture, sterilization, and use thereof.

SUMMARY OF THE DISCLOSURE

Without limiting the various aspects of the present subject matter described herein, and in accordance with one aspect of the present disclosure, a connector for providing sterile access to a flexible container is provided that comprises a tubular member having a first portion and a second portion, each of the first portion and the second portion having an open end. The first portion and second portion are joined to each other by a frangible segment, with each of the first portion and the second portion having a gripable surface associated therewith that is configured to facilitate the application of torsional force to the tubular member at the frangible segment. Upon the application of a sufficient amount of torsional force, the frangible segment will break, permitting the first and second portions to be separated from each other.

In accordance with another aspect of the disclosure, one of the first and second portions includes a seal or cover on the end thereof while the other includes a pierceable membrane and is configured to have a flexible container attached thereto.

In accordance with a further aspect of the disclosure, the gripable surfaces on the first and second portions have a generally planar configuration and comprise one or more reinforcing elements that serve to rigidify the gripable surfaces.

In accordance with another aspect of the disclosure, the frangible segment of the connector has a reduced wall thickness relative to the wall thicknesses of the first and second portions. In accordance with a further aspect of the disclosure, the first portion of the connector includes a radially-outwardly extending flange or collar adjacent the frangible segment and a tubular extension configured to receive a spike extending past the flange, with the tubular extension having an outside diameter smaller than the inside diameter of the second portion of the connector. The tubular extension extends beyond the flange or collar into the second portion, with the flange having a diameter that is greater than the extent to which the tubular extension protrudes beyond the flange. Preferably, the diameter of the flange is at least approximately three times the length of the tubular extension.

In accordance with another aspect of the disclosure, the tubular extension comprises an inside surface configured to engage the spike during penetration of the piercreable membrane, with the inside surface of the tubular extension having a surface finish roughness for reducing friction.

In accordance with a further aspect of the disclosure, the first portion of the connector includes a first segment proximal to the pierceable membrane having a first inside diameter and a second segment distal to the pierceable membrane having a second inside diameter less than the first inside diameter, and the pierceable membrane has a diameter substantially the same as the first inside diameter.

In accordance with another aspect of the disclosure, a flexible container comprising a flexible wall defining an interior chamber is provided that incorporates a sterile connector having any and all of the above-referenced characteristics.

DETAILED DESCRIPTION

A more detailed description of the sterile connector in accordance with the present disclosure is set forth below. However, it should be understood that the description below of a specific device is intended to be exemplary, and not exhaustive of all possible variations or applications. Thus, the scope of the disclosure is not intended to be limiting, and should be understood to encompass variations or embodiments that would occur to persons of ordinary skill.

In accordance with the disclosure, a sterile connector for providing access to the interior of a container for medical fluids, typically a flexible plastic bag, is provided. The connector is welded or otherwise secured to the flexible bag along its periphery and allow for selected access to the interior of the bag.

The connector includes a membrane in the interior thereof that can be pierced by a spike, needle, or other access device to thereby allow fluid communication with the interior of the bag. The connector is provided with opposed pairs of gripable members or tabs that are separated by a frangible segment. Access to the pierceable membrane is achieved by grasping one pair of tabs in each hand and twisting in the opposite direction to apply a torsional force to the frangible segment and thus sever the connector along the line of weakness between the tabs.

The tabs are provided with reinforcing elements that provide for their torsional rigidity and also serve to reduce the amount of material required for the tabs. After severing the connector along the line of weakness and separating the two portions, the pierceable membrane is exposed so that it may be ruptured to permit access to the interior of the bag. The portion of the connector remaining with the bag comprises the port for receiving the spike for penetrating the membrane. The port is formed with a collar or flange, beyond which a tubular member extends. The diameter of the flange or collar is greater than the length of the tubular member. This configuration helps to ensure that, once the cover is removed, the free end of the port that receives the spike will be less likely to touch a potentially-contaminated surface if the bag were to be set on such a surface prior to the time the membrane is broken.

Figure 1:
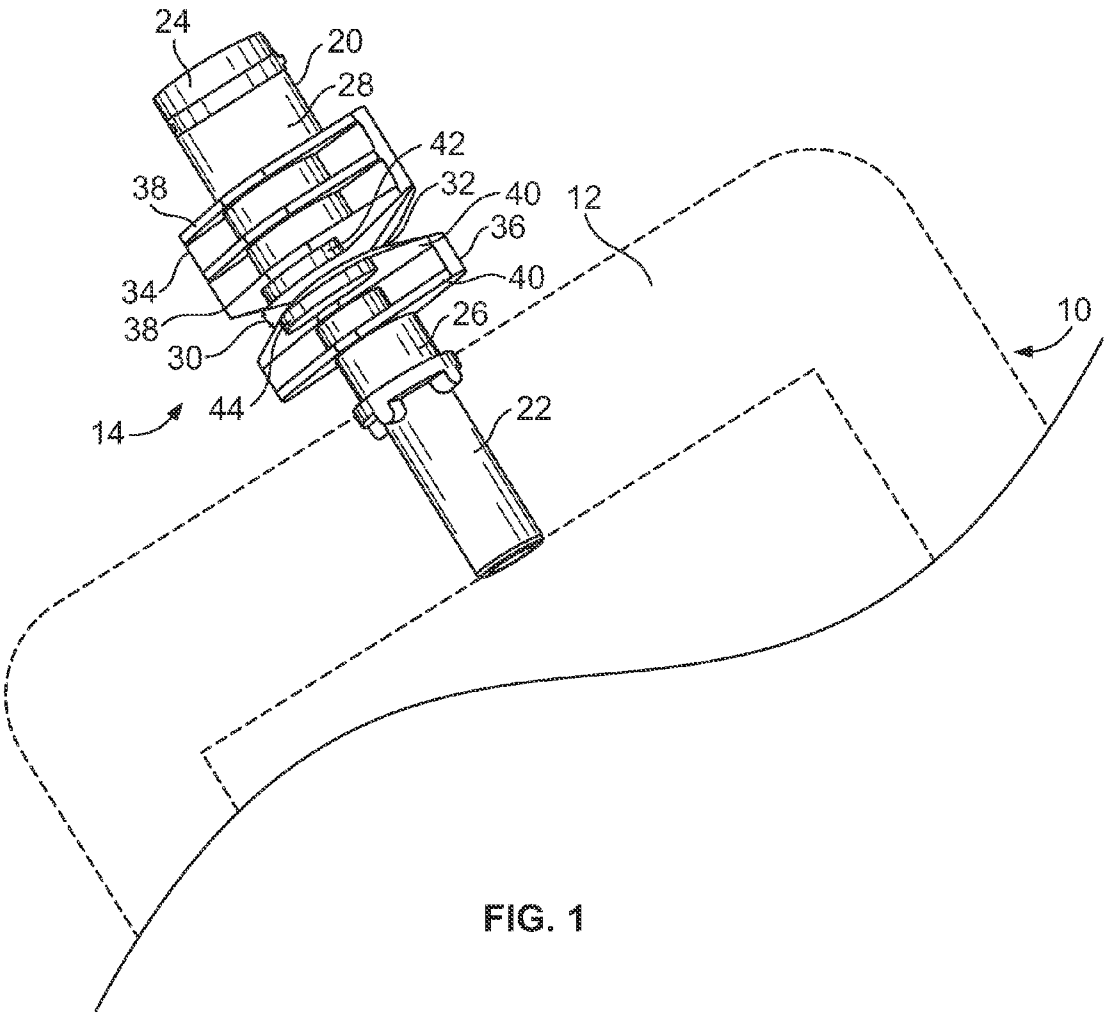
FIG. 1 is a perspective view of a connector according to the present disclosure shown in combination with a portion of a flexible container (shown in dotted lines).

Turning to the drawings, there is seen in FIG. 1 a portion of a container or bag 10 configured to receive a medical fluid. The bag 10 typically is made of superimposed films, preferably made of a biocompatible and preferably autoclavable material suitable for use in the medical field. Suitable materials may include PVCs, polyolefins, including polyolefin blends, and, preferably, non-DEHP materials. However, the selection of materials is not limiting provided they have the required physical properties. The opposed films (i.e., the container walls) are sealed together about their common periphery 12 by, e.g., welding, the application of RF energy, adhesive, etc. The bag 10 includes a sterile openable access port, i.e., sterile connector 14, typically comprising a plastic material that is compatible from a sealing and sterilization standpoint with the material of bag 10. The connector 14 may be made by, e.g., well-known injection molding processes. The material of the connector and the container are such that the connector may be secured in the peripheral seal of the container by RF sealing, impulse, or thermal joining operations, and sterilized by the application of steam, electron beam ("E-beam"), or gamma radiation sterilization. E-beam and gamma sterilization are preferred if the container is empty of solutions. Again, the selection of materials is not limiting provided they have the required physical properties.

The connector 14 is of a generally tubular configuration, with a hollow interior 16 (seen in FIG. 3) that provides the fluid pathway through the connector 14. A pierceable or ruptureable membrane 18 (also seen in FIG. 3) is located intermediate the two ends 20, 22 of the connector. The free end 20 of the connector, that is, the portion that extends outwardly from the bag, includes a cover or seal 24 (FIGS. 1-2) to maintain the sterility of the fluid pathway prior to use. The cover 24 is preferably manufactured separately from the remainder of the connector 14, but of the same or similar material, and is secured thereto by, e.g., welding. RF energy, adhesive, so as to create a hermetic seal to maintain the sterility of the interior 16 of the connector 14.

In order to gain access to the interior of the connector, the connector is configured so that, with the application of a sufficient torsional force, the connector fractures into two pieces to allow access to the hollow interior 16 of the connector 14 and to expose the pierceable membrane 18. Preferably, the material from which connector 14 is made has a hardness of from approximately 60 to 90 Shore A Durometer, and a torsional modulus of from approximately 700 psi to 900 psi. The connector fractures into a port portion 26, within which is the membrane 18, and a cover portion 28. In a preferred embodiment, the port portion 26 complies with ISO standards 3826, and has a wall thickness of from approximately 0.015 in. to 0.050 in., which facilitates RF or other sealing/joining operations to secure the connector 14 to the flexible sheeting comprising the container 10. The cover portion 28 preferably has a wall thickness of from approximately 0.020 in. to 0.070 in. This allows sufficient moist heat (steam) penetration to sterilize the hollow interior 16 of connector 14 between the cap 24 and the membrane 18.

Figure 3:
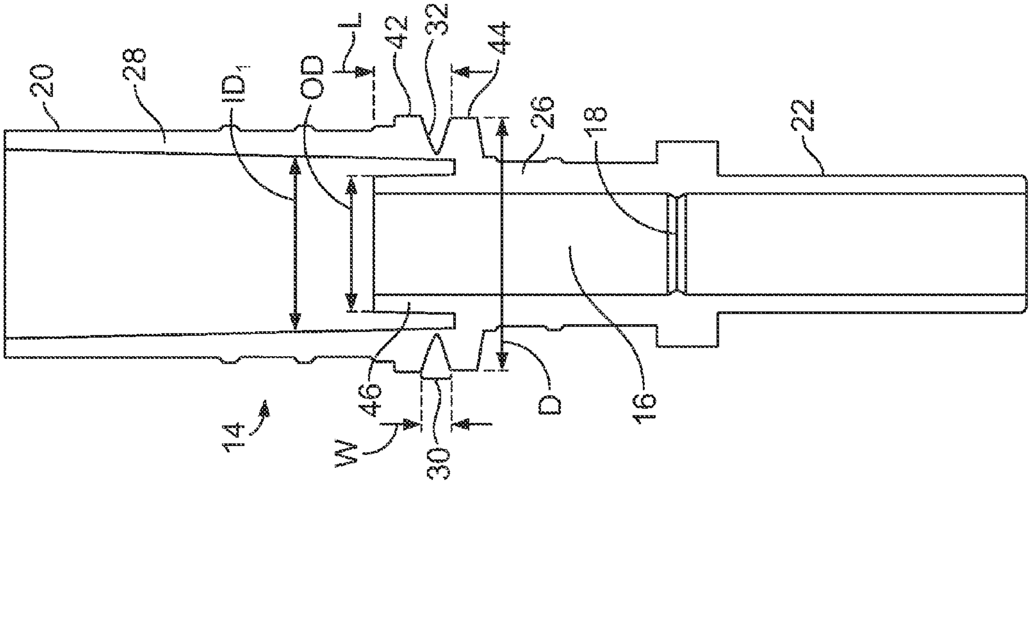
FIG. 3 is a cross-sectional view of the connector along a plane generally perpendicular to the plane defined by the gripable surfaces of the connector.

To facilitate the removal of the cover portion 28, the connector 14 is provided with a frangible region or segment 30 intermediate the port portion 26 and the cover portion 28 of the connector. The frangible segment 30 may be created by having a reduced wall thickness for the connector 14 at the desired fracture line. As best seen in FIG. 3, the connector may be formed with a circumferentially-extending, V-shaped notch 32 to provide the fracture line. In a preferred embodiment, the frangible segment 30 has a width, W, of from approximately 0.005 in. to 0.020 in. wide, while the wall thickness of the connector 14 at the notch 32 is from approximately 0.004 in. to 0.020 in. Other configurations for providing the frangible segment 30 may also be used, including other shapes for the notch, or by performing a material treatment to otherwise weaken the connector 14 at the frangible segment 30.

Figure 2:
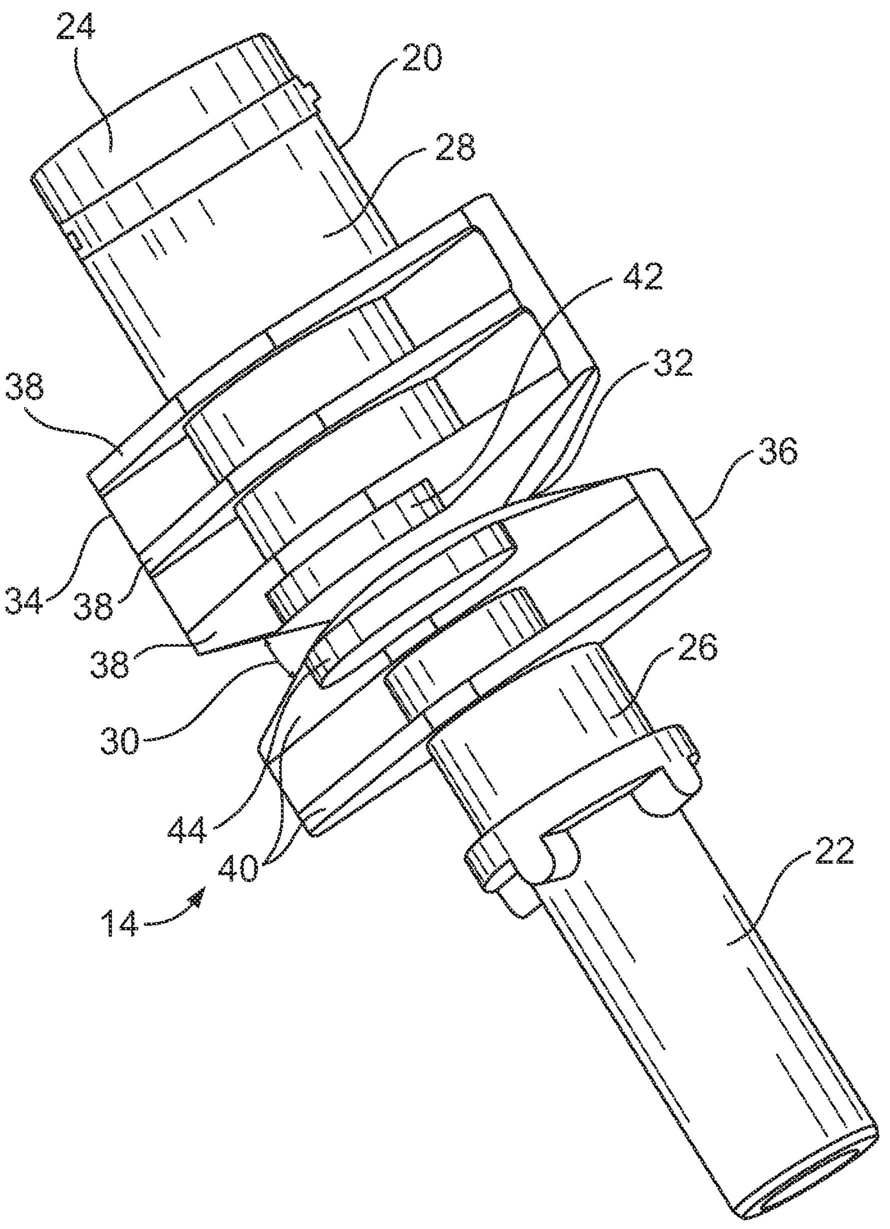
FIG. 2 is a perspective view of the connector of FIG. 1.
Figure 4:
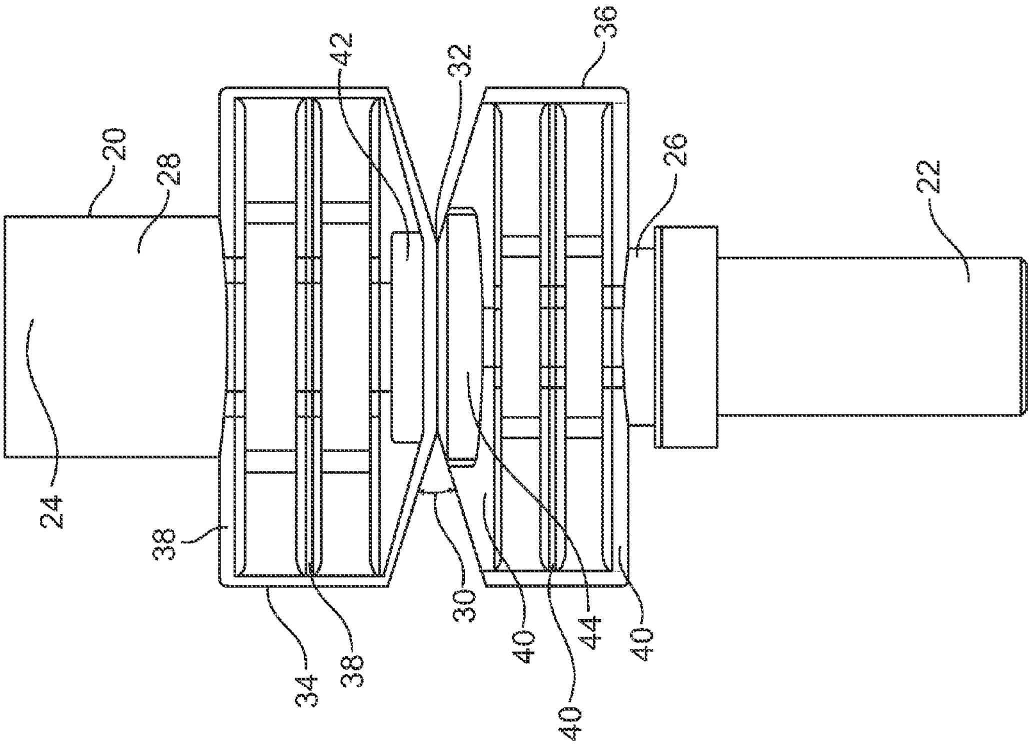
FIG. 4 is a plan view of a first alternate embodiment of a connector according to the present disclosure.

In keeping with one aspect of the disclosure, the connector 14 is provided with surfaces 34, 36 on opposite sides of the frangible segment 30 that are ergonomically configured to be held between the fingers of the hands of a user to facilitate the application of the torsional force to the connector 14 at the frangible segment 30. Preferably, a ¼ turn in opposite directions of the surfaces 34, 36 (i.e., approximately 90° of relative rotation between the portions 26, 28) will create a sufficient torque to break the frangible segment. As seen in the drawings, the gripable surfaces 34, 36 extend from the connector 14 in a wing-like fashion. The gripable surfaces 34, 36 may be of different widths, as seen in FIGS. 1-3, or may be of approximately equal width, as seen in FIG. 4.

Each of the surfaces 34, 36 is configured to have one or more reinforcing elements. The reinforcing elements serve to impart rigidity to the gripable surfaces so that they tend not to bend or otherwise deform when the torsional force is applied. The reinforcing elements may be raised ribs, such as the ribs 38, 40 shown in FIGS. 1 and 2. In addition to increasing the rigidity of the wings 34, 36, the raised ribs 38, 40 also improve their gripability, while at the same time reducing the quantity of material required to form the wings. Further, one or both of the wings 34, 36 may include a collar or flange-like configuration 42, 44 adjacent to frangible segment 30. The collars 42, 44 add to the rigidity of the connector 14 so that it is less likely to collapse or otherwise deform when a torsional force is applied.

In keeping with another aspect of the disclosure, the connector 14 is configured so that, once the frangible segment 30 is broken and the cover portion 28 of the connector removed, the port 26 that receives the spike or hypodermic needle has a reduced likelihood of inadvertently contacting a non-sterile surface. To this end, the tubular extension 46 forming the port 26 for the spike has an outside diameter or dimension, OD, that is less than the inside diameter or dimension, $ID_1$, of the cover portion 28, thus providing a space between the two. This physical separation between the port and the cover helps to ensure no direct contact by the user to a non-sterile surface when accessing the port.

In addition, the collar or flange 44 associated with the tubular extension 46 is dimensioned so that it has a diameter, D, greater than the length, L, of the tubular extension 46. Thus, if the bag 10 is placed on a surface after the cover 28 is removed, the tubular extension 46 is less likely to contact the surface. Instead, the connector 14 will rest on the flange 44 with the free end of the tubular extension 46 spaced away from the surface. Preferably, the diameter, D, of the collar or flange 44 is at least about a three times the length, L, of the tubular extension 46.

Figure 5:
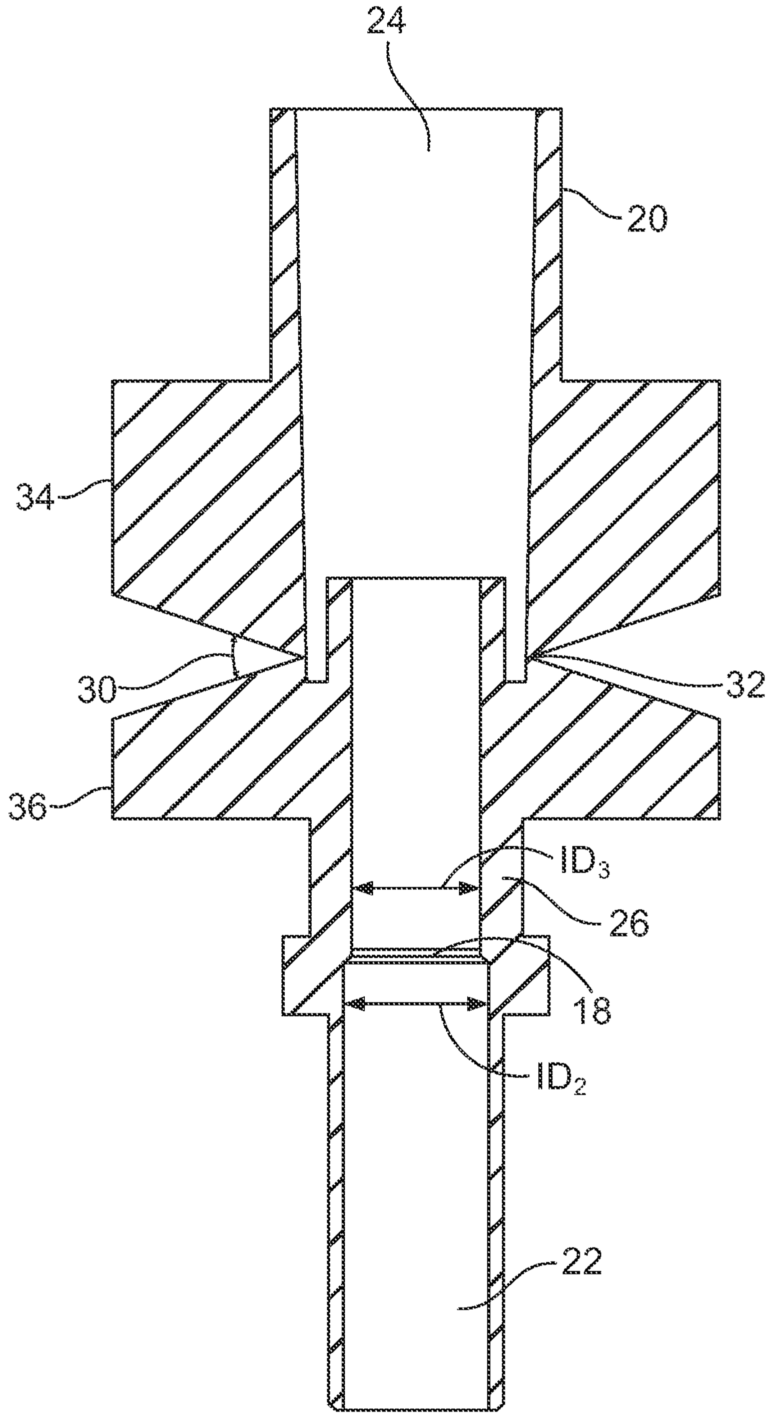
FIG. 5 is a cross-sectional view of a second alternate embodiment of a connector according to the present disclosure.

With reference to FIG. 5, the inside diameter $ID_2$ of the segment of end portion 22 of the connector 14 below or distal to the pierceable membrane 18 is greater than the inside diameter $ID_3$ of the segment of end portion 22 above or proximal to the pierceable membrane 18, and the membrane 18 has a diameter substantially the same as $ID_2$. This provides sufficient space for the ruptured membrane 18 when it is displaced into the distal segment of the end portion 22 during spiking, and thus helps to control the forces required for spike insertion. Preferably, $ID_2$ is greater than $ID_3$ by a minimum of one-times (1×) the thickness of the pierceable membrane 18. Additionally, the inside surface of end portion 22 proximal to the membrane 18 is provided with a finish for enhanced control of spike insertion and retention forces. For example, the inside surface of end portion 22 may be provided with a roughened surface, such as a surface finish roughness of up to finish standard SPI-SPE D-3 #24 oxide blast, or equivalent, to reduce the insertion force required for spiking by reducing the contact area (and thus the friction) between the interior of the port and the spike.

Thus, an improved sterile connector and medical container including such a connector have been disclosed. The description above is intended for illustrative purposes only, and is not intended as to the scope of the disclosure to any specific apparatus or device herein.

The invention claimed is:

1. A connector for providing sterile access to a flexible container for receipt of a medical fluid comprising:

a tubular member having a first portion and a second portion, each of the first portion and second portion having an open end;

the first portion and the second portion joined to each other by a frangible segment;

each of the first portion and the second portion having a generally planar gripable surface associated therewith comprising raised ribs configured to facilitate the application of torsional force to the tubular member at the frangible segment;

the first portion having a seal on the end thereof and the second portion having a pierceable membrane and being configured to have the flexible container attached thereto, the gripable surface associated with the second portion being positioned thereon so as to be exterior to the flexible container;

the second portion includes a radially-outwardly extending flange adjacent the frangible segment and a tubular extension configured to receive a spike extending beyond the flange and having an outer diameter smaller than the inside diameter of the first portion, the tubular extension extending past the frangible segment into the first portion, the flange having a diameter that is greater than the length of the tubular extension; and the tubular extension comprises an inside surface configured to receive and engage a spike to penetrate the pierceable membrane, the inside surface having a roughened surface finish for reducing friction between the inside surface and a spike received therein.

2. The connector of any of claim 1 in which the frangible segment has a reduced wall thickness relative to the first portion and second portion.

3. The connector of claim 1 wherein the second portion includes a first segment proximal to the pierceable membrane having a first inside diameter and a second segment distal to the pieceable membrane having a second inside diameter greater than the first inside diameter.

4. The connector of claim 1 in which the diameter of the flange is at least approximately three times the length of the tubular extension.

5. The connector of claim 1 further comprising a flexible container sealed to the first portion.

6. A flexible container comprising:

opposed flexible walls defining an interior chamber;

a connector for providing sterile access to the interior chamber of the flexible container, the connector comprising:

a tubular member having a first portion and a second portion, each of the first portion and second portion having an open end;

the first portion and the second portion joined to each other by a frangible segment;

each of the first portion and the second portion having a generally planar gripable surface associated therewith comprising raised ribs configured to facilitate the application of torsional force to the tubular member at the frangible segment;

the first portion of the connector having a seal on the end thereof and the second portion having a pierceable membrane having the opposed walls of the flexible container attached thereto, the gripable surface associated with the second portion being positioned thereon so as to be exterior to the flexible container;

the second portion includes a radially outwardly extending flange adjacent the frangible segment and a tubular extension configured to receive a spike extending beyond the flange and having an outer diameter smaller than the inside diameter of the first portion, the tubular extension extending past the frangible segment into the first portion, the flange having a diameter that is greater than the length of the tubular extension; and the tubular extension comprises an inside surface configured to receive and engage a spike to penetrate the pierceable membrane, the inside surface having a roughened surface finish for reducing friction between the inside surface and a spike received therein.

7. The flexible container of claim 6 in which the frangible segment of the connector has a reduced wall thickness relative to the first portion and second portion.

8. The flexible connector of claim 6 wherein the second portion includes a first segment proximal to the pierceable membrane having a first inside diameter and a second segment distal to the pierceable membrane having a second inside diameter greater than the first inside diameter.

9. The flexible connector of claim 6 in which the diameter of the flange on the connector is at least approximately three times the length of the tubular extension.

* * * * *